(12) United States Patent
Grendze et al.

(10) Patent No.: US 7,151,181 B2
(45) Date of Patent: Dec. 19, 2006

(54) PROCESS FOR THE PREPARATION OF 3,5-DIETHYL-1,2-DIHYDRO-1-PHENYL-2-PROPYLPYRIDINE

(75) Inventors: Martin Grendze, Indianapolis, IN (US); Ramiah Murugan, Indianapolis, IN (US); L. Mark Huckstep, Avon, IN (US); Charles R. Hopper, Avon, IN (US)

(73) Assignee: Reilly Industries, Inc., Indianapolis, IN (US)

( * ) Notice: Subject to any disclaimer, the term of this patent is extended or adjusted under 35 U.S.C. 154(b) by 0 days.

(21) Appl. No.: 11/351,783

(22) Filed: Feb. 10, 2006

(65) Prior Publication Data
US 2006/0178517 A1    Aug. 10, 2006

Related U.S. Application Data

(60) Provisional application No. 60/651,711, filed on Feb. 10, 2005, provisional application No. 60/651,706, filed on Feb. 10, 2005.

(51) Int. Cl.
*C07D 211/02*    (2006.01)

(52) U.S. Cl. .................................................... 546/249
(58) Field of Classification Search ................. 546/249
See application file for complete search history.

(56) References Cited

OTHER PUBLICATIONS

Cindric, Marina et. al., "Hexanuclear complexes of molybdenum (V) containing [Mo6O12(OCH3)4(acac)3]-anion", Polyhedron 19 (2000), pp. 1471-1478.*

* cited by examiner

*Primary Examiner*—Thomas McKenzie
*Assistant Examiner*—Binta Robinson
(74) *Attorney, Agent, or Firm*—Homer W. Faucett, III; Ice Miller LLP

(57) ABSTRACT

Methods are provided for improving production of 3,5-diethyl-1,2-dihydro-1-phenyl-2-propylpyridine (DHP). In one illustrative embodiment, the methods involve controlling the rate of reaction and temperature of the reaction during formation of DHP. In another illustrative embodiment, the methods involve neutralizing the acid catalyst subsequent to DHP formation.

18 Claims, No Drawings

US 7,151,181 B2

PROCESS FOR THE PREPARATION OF 3,5-DIETHYL-1,2-DIHYDRO-1-PHENYL-2-PROPYLPYRIDINE

PRIORITY

This application claims priority to U.S. Provisional Patent Application Nos. 60/651,706 and 60/651,711, entitled Improved Process for the Production of 3,5-Diethyl-1,2-Dihydro-1-Phenyl-2, both filed Feb. 10, 2005, and incorporated herein by reference.

BACKGROUND

1. Field of the Invention

The present application relates generally to the production of amine-aldehyde condensation products, illustratively 3,5-diethyl-1,2-dihydro-1-phenyl-2-propylpyridine, and methods for improving production.

2. Description of Related Technology

Reactive fluid compositions, otherwise known as tough acrylic adhesive compositions or second generation acrylics, are well known adhesive systems. Typically, these are two-part systems that offer the advantages of rapid cure, high strength, and good shelf life.

The first part of these adhesive compositions generally is a polymer-in-monomer solution. Typically, this first part includes and vinyl or acrylic monomers such as methyl methacrylate, and chlorosulfonated polyethylene. Chlorosulfonated polyethylene is a reaction product of a linear or branched polyethylene and sulfonyl chloride. One example of chlorosulfonated polyethylene is HYPALON™ (E. I. DuPont De Nemours' & Co.). Illustrative polymer-in monomer solutions are disclosed in U.S. Pat. Nos. 3,890,407, 3,962,372, 4,106,971 and 4,112,013, herein incorporated by reference.

The second main component of the adhesive compositions is usually a mixture or solution of activators, promoters, initiators, and free radical generators, all of which are discussed in the above-mentioned patents, already incorporated by reference. Examples of typical prior art free radical generators include organic peroxides, hydroperoxides, peresters, persalts, and peracids. Illustrative initiators include amines, such as N,N-dimethylaniline, and illustrative promoters include transition metals such as manganese or nickel.

Amine-aldehyde condensation products are often employed as the activator. Typically, these activators are the products of the reaction between an aliphatic aldehyde (usually $C_{1-12}$) and an aromatic amine. U.S. Pat. No. 3,890,407 lists illustrative amines and aldehydes useful as condensation reactants. One commonly used activator is the condensation product of the reaction between butyraldehyde and aniline. Commercial sources of the butyraldehyde aniline condensation product include DuPont 808 (E. I. DuPont De Nemours & Co.), VANAX® 808 (RT Vanderbilt Company), Vulkacit 576 (Bayer Corp.), Accelerator 40B (Akrochem Corp.), and NOCCELER 8 (Ocuchishiko Chemical). It is understood that the term "activator" is commonly used interchangeably with the terms "accelerator" and "primer."

It is known that 3,5-diethyl-1,2-dihydro-1-phenyl-2-propylpyridine (DHP) is the main active ingredient resulting from the condensation reaction of butyraldehyde and aniline. However, the condensation reaction is not a simple addition reaction. Rather, a variety of side reactions occur, with a variety of resulting products. Many such side reactions are discussed in U.S. Pat. Nos. 1,780,334, 1,908,093 and 2,704,750, herein incorporated by reference.

The first known preparation of DHP was reported in Craig, JACS, Vol. 70, pp, 1624–1629 (1948), herein incorporated by reference. The Craig reference misidentified the compound as N-phenyl-3,5-diethyl-2-propyl-1,4-dihydropyridine, but DHP has subsequently been shown to be the principle component of the reaction mixture. As many of the components of the crude mixture were then unknown, the crude DHP mixture has become known as "butyraldehyde aniline condensation product." There has been surprisingly little information on improvements in the preparation of DHP since the original 1948 publication. Instead, various efforts have focused on distilling DHP from the other components of butyraldehyde aniline condensation product. See U.S. Pat. No. 4,450,050. A commercially available purified DHP, PDHP™ Adhesive Activator (Reilly Industries, Inc.) comprises 85% or more DHP and is produced from purifying a crude butyraldehyde aniline condensation mixture.

One disadvantage to many present adhesive systems that use aldehyde-amine condensation products as surface activators is that the adhesive compositions do not readily adhere to the oily surface of the activator. The adhesive tends to slip or "skate" along the surface of the activator and to flow off the bond area prior to assembly. This "skating" of the adhesive off the activated surface is believed to be caused by a variety of substances that prevent proper wetting and interaction of the adhesive with the surface to be bonded. Due to the nature of the condensation reaction used to make amine-aldehyde activators, many other compounds are formed that do not enhance the activator's ability to function as an accelerator and contribute to the polymerizable portion (polymer-in-monomer part) of the adhesive composition sliding off the surface of an activator-coated part. The result is poor wetting of the surface by the adhesive, resulting in low bond strength. Additionally, many of these noncontributing products impart an obnoxious odor and a brown staining color that can require ventilation and precautionary handling measures and can cause aesthetic imperfections in the surfaces to be bonded. The polymerizable portion of the adhesive composition is generally a clear, viscous material, but when in contact with the activated surface takes on the brown dirty color of the activator.

While highly purified DHP is desirable, purification can be costly, and highly purified DHP is significantly more expensive than its crude counterpart products. Yet materials such as VANAXφ 808, Vulkacit 576, Accelerator 40B, and NOCCELER 8 contain about 40% or less DHP. Condensation methods that result in a product having a greater percentage DHP are desired. Also desired are condensation products that can be purified more readily. More consistent activity can be achieved by higher DHP concentrations and by a reduction in the number and concentration of byproduct impurities that can interfere with the polymerization process. It is also desirable to reduce the levels of impurities that are considered to be hazardous (toxic, flammable, corrosive, etc.).

SUMMARY OF THE INVENTION

Accordingly, the present invention is directed to methods for improving production of 3,5-diethyl-1,2-dihydro-1-phenyl-2-propylpyridine (DHP). In one aspect of the invention, improved yields of DHP are obtained by controlling the rate of reaction and temperature while in the presence of the acid catalyst. The rate of reaction is controlled by allowing the reaction to proceed at a lower temperature for a period of time prior to raising the temperature to a higher reaction temperature. In one illustrative example, the reaction mixture is heated slowly to 40–45° C. and held for one hour prior to heating to 75° C. for five hours, and only then heated to reflux.

In a second aspect of the invention, improvement in DHP production is obtained by neutralizing the acid catalyst subsequent to DHP formation. Illustratively, prior to distillation the acid catalyst is neutralized using sodium carbonate, but other bases may be used as well. By neutralizing the acid catalyst, decomposition of DHP is minimized when the reaction is heated for distillation of the DHP.

Another aspect of the present application is directed to methods for preparing 3,5-diethyl-1,2-dihydro-1-phenyl-2-pr (DHP) in improved yields. In one aspect of the invention, the traditional order of reagent addition is altered. In this aspect, aniline is first added to the butyraldehyde, and then the acid catalyst is added subsequently.

Combinations of these methods are also within the scope of this application.

Other objects and advantages of the subject matter of this application will be apparent to those skilled in the art from the following detailed description, taken in conjunction with the appended claims.

DETAILED DESCRIPTION 3,5-Diethyl-1,2-dihydro-1-phenyl-2-propylpyridine (DHP) has the following structure:

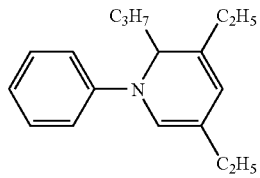

Methods for the production of DHP can be found in the Craig reference discussed above, which is incorporated herein by reference. Changes in these methods, as discussed herein, have resulted in improved yields of DHP and improved recovery of DHP in subsequent purification.

In Example I below, DHP is produced by methods consistent with the teaching of the Craig reference. Two main changes were made between Example I and Example II. The first main change involves controlling the temperature of the mixture while in the presence of the acid catalyst. In each of the examples, the mixture was created at 20–25° C., stirred for an hour at this temperature, and then subsequently heated. In Example I, the mixture was heated to 75° C., held for two hours and subsequently heated to reflux (about 90° C.) for five hours. In Example II, the mixture is heated slowly to 40° C., held for one hour, heated to 75° C. for five hours, and subsequently heated to reflux. In Example III, it has been found that heating to a reaction temperature of 75° C. prior to heating to reflux allows for easier recovery of DHP during subsequent purification. Further, it has been found that holding the mixture at a lower temperature for a period of time prior to heating to 75° C. improves yield of DHP. Illustratively, that period of time is at least 15 minutes, illustratively at least 30 minutes. In the examples, a hold of approximately one hour provided for improved yield. Illustratively, this hold is at a temperature of no more than 50° C., illustratively 40–45° C.

The second change involves the addition of a base, illustratively sodium carbonate, prior to distillation. The base neutralizes the acetic acid, thereby reducing degradation of the DHP while at the high distillation temperatures, and leading to better yield. While sodium carbonate is used in Examples II and III, other bases may be used, including but not limited to sodium or potassium carbonate, sodium or potassium bicarbonate, and sodium or potassium hydroxide.

The following chemicals were used in the following examples:

Acetic acid, Fisher Chemical, glacial, 99.9%
Aniline, Acros Chemical, ACS reagent grade
Butyraldehyde, Acros Chemical, 99%
Sodium carbonate, Aldrich Chemical, 99.5%

EXAMPLE I

DHP was prepared using methods consistent with the methods in the literature. A 1000 mL four neck flask was equipped with a mechanical stirrer, a reflux condenser, a thermometer, and an addition funnel. An ice-water bath was used to cool the flask as needed. The flask was charged with 86 g de-ionized water, 9.8 g (0.16 mole) acetic acid, and 216 g (3.0 mol) butyraldehyde. With cooling and stirring, 60 g (0.64 mole) aniline was added over a 35-minute period while maintaining the reaction temperature at 20° C. The reaction mixture was stirred for one hour at less than 25° C. The reaction mixture was then heated to 75° C. and held for two hours. Finally, the reaction mixture was heated to reflux (~90° C.) and was held for five hours. The reaction mixture was cooled and the layers were separated. The top, organic layer was distilled through a 14" packed column under reduced pressure. The fraction taken at a head temperature of 140–143° C. and 5 mm Hg pressure weighed 104 grams and was analyzed to contain 73% DHP for an overall yield of 46%.

EXAMPLE II

A 1000 mL flask was equipped in the same matter as above. With stirring and cooling, the flask was charged with 433 grams (6.0 mole) butyraldehyde, 120 grams (1.3 mole) aniline, and 9.8 grams acetic acid (0.16 mole). The mixture was maintained at 20–25° C. as each reactant was added, after which the reaction temperature slowly increased to 40° C. The reaction mixture was allowed to stir for one hour at 40° C. then heated to 75° C. and held for five hours. A solution of 10% aqueous sodium carbonate (100 mL) was added to the flask and the reaction mixture was heated to reflux and held for additional five hours. The reaction mixture was cooled and the layers were separated. The top, organic layer was distilled through a 14" packed column under reduced pressure. The product cut was taken at a head temperature of 140–143° C. and 4 mm Hg pressure weighed 219 grams was analyzed to contain 89% DHP, which translates to an overall chemical yield of 59%.

EXAMPLE III

Several parameters were changed between Example I and Example II. To isolate the effects of each parameter, a series of runs was made wherein in each run only one parameter was changed. As shown in Table 1, runs were made to compare the reaction temperature after completion of the addition of the reactants and the effect of neutralizing the reaction mixture prior to refluxing. All reported yields are based on the weight of the recovered top layer from the reaction mixtures and a gas chromatograph (GC) analysis of the top layer. Thus, these are chemical yields of DHP made and not isolated recovered yields.

TABLE 1

| | Run # | | | | |
|---|---|---|---|---|---|
| | 1<br>5 hr @ reflux | 2<br>5 hr @ 75° C. | 3<br>1 hr @ <45° C.<br>5 hr @ 75° C. | 4<br>5 hr @ 75° C.<br>5 hr @ reflux | 5<br>5 hr @ 75° C.<br>5 hr @ reflux |
| Reactants: | | | | | |
| Butyraldehyde | 216.3 g<br>(3.0 mole) | 216.3 g<br>(3.0 mole) | 216.3 g<br>(3.0 mole) | 216.3 g<br>(3.0 mole) | 216.3 g<br>(3.0 mole) |
| Aniline | 60.0 g<br>(0.64 mole) | 60.0 g<br>(0.64 mole) | 60.0 g<br>(0.64 mole) | 60.0 g<br>(0.64 mole) | 60.0 g<br>(0.64 mole) |
| Acetic Acid | 9.8 g<br>(0.16 mole) | 9.8 g<br>(0.16 mole) | 9.8 g<br>(0.16 mole) | 9.8 g<br>(0.16 mole) | 9.8 g<br>(0.16 mole) |
| GC Analysis of<br>Reaction Mixture: | | | | | |
| Butyraldehyde, % | 5.97 | 8.54 | 9.32 | 2.53 | 5.32 |
| 2-Ethyl-2-hexenal, % | 25.12 | 22.71 | 20.66 | 29.14 | 25.52 |
| Aniline | 0.02 | 0.02 | 0.01 | 0.04 | 0.04 |
| DHP, % | 48.76 | 48.83 | 52.66 | 49.24 | 49.45 |
| Chemical Yield DHP<br>(%, GC) | 70.3 | 70.9 | 76.0 | 69.8 | 70.2 |
| Comments | heated at reflux for 5 hrs. | heated at 75° C. for 5 hrs. | held at <45° C. for 1 hr; heated at 75° C. for 5 hrs. | heated at 75° C. for 5 hrs; added Na$_2$CO$_3$ soln, heated at reflux for 5 hrs. | heated at 75° C. for 5 hrs; then heated at reflux for 5 hrs. |

Runs 1, 2, and 3 are a comparison of reaction temperature after the addition of the reactants. In run 1 the reaction was immediately heated to reflux, in run 2 the reaction was immediately heated to 75° C., and in run 3 the reaction was held at <45° C. for one hour before heating to 75° C. No difference in chemical yield was seen between runs 1 and 2. However, subsequent recovery of DHP from the crude mixture was greater with DHP prepared according to run 2 (data not shown), perhaps due to a decrease in the production of other compounds that make purification more difficult. In run 3, an improvement in the chemical yield of DHP was seen in addition to the improvement in recovery during subsequent purification. Thus, it has been found that holding the reaction mixture at a lower temperature for a period of time is beneficial to formation and purification of DHP. Without being bound to any particular theory, it is thought that the lower temperature may suppress the formation of other products that consume materials that could have been converted to DHP.

Runs 4 and 5 are comparisons of the effect of base neutralization prior to refluxing on DHP yield. Previous work had shown DHP to decompose under acidic conditions when heated, especially at high temperature. By neutralizing the acidic catalyst before heating to reflux temperatures, decomposition of DHP can be suppressed. No difference in DHP chemical yield was seen in runs 4 and 5 but, again, subsequent recovery of DHP from the crude mixture was greater with DHP prepared according to run 4 than with run 5 (data not shown). Neutralization with a base allows the excess butyraldehyde to be reduced via base-catalyzed self-condensation, which is faster than acid catalyzed self-condensation. Also, the base neutralized run appeared to give improved layer separation. The top layer was relatively clear as compared to the other runs in which the top layers were cloudy. It was also noted that top layers from the non-neutralized runs would form small water droplets or layers in the sample bottles after standing for a few days. Neutralization of the acid catalyst is particularly useful when the product is distilled under high temperatures. Distillation of a neutralized DHP crude mixture produces fewer decomposition products and leads to increased recovered yields of purified DHP.

The foregoing detailed description is given for clearness of understanding only, and no unnecessary limitations should be understood therefrom, as modifications within the scope of the invention will be apparent to those skilled in the art.

EXAMPLE IV

Example IV relates to In run 1 below, DHP is produced by methods consistent with the teaching of the Craig reference, wherein the acetic acid is mixed with the butyraldehyde, and the aniline is added subsequently. In run 2, this order has been altered, wherein the aniline and butyraldehyde are mixed, and the acetic acid is subsequently added to the mixture. It has been found that this change in the sequence leads to more consistent yields of DHP.

The following chemicals were used in Example IV:

Acetic acid, Fisher Chemical, glacial, 99.9%

Aniline, Acros Chemical, ACS reagent grade

Butyraldehyde, Acros Chemical, 99%

A 1000 mL four neck flask was equipped with a mechanical stirrer, a reflux condenser, a thermometer, and an addition funnel. An ice-water bath was used to cool the flask as needed. The flask was charged with the reactants while maintaining the reaction temperature at 20° C. (amounts shown in Table 2 in moles). The reaction mixture was stirred for one hour at less than 25° C. The reaction mixture was then heated to reflux (~90° C.) and was held for five hours. The reaction mixture was cooled and the layers were separated. The top, organic layer was distilled through a 14" packed column under reduced pressure. The fraction taken at a head temperature of 140–143° C. and 5 mm Hg pressure was analyzed by gas chromatography.

TABLE 2

| | Run # | |
|---|---|---|
| | 1<br>5 hr @ reflux | 2<br>5 hr @ reflux |
| Reactants: | | |
| Butyraldehyde | 216.6 g (3.0 mole) | 216.3 g (3.0 mole) |
| Aniline | 60.0 g (0.64 mole) | 60.0 g (0.64 mole) |
| Acetic Acid | 9.8 g (0.16 mole) | 9.8 g (0.16 mole) |
| GC Analysis of<br>Reaction Mixture: | | |
| Butyraldehyde, % | 5.71 | 5.97 |
| 2-Ethyl-2-hexenal, % | 26.25 | 25.12 |
| Aniline | 0.02 | 0.02 |
| DHP, % | 48.36 | 48.76 |
| Chemical Yield DHP (%, GC) | 70.0 | 70.3 |
| Comments | Added AcOH to butanal then aniline; heated at reflux for 5 hrs. | Added aniline to butanal then AcOH; heated at reflux for 5 hrs. |

Runs 1 and 2 compare the effect of order of addition of the reactants on the yield of DHP. As can be seen in the table, the order of addition had no negative effect on the yield of DHP in these lab runs. While no significant positive effect was seen either, the time period between addition of the acetic acid and aniline was relatively short, and, with the slow addition time, controlling the reaction temperature was not difficult. In bench runs, little effect is seen in reversing the order of addition of the reactants. However, under production conditions, the time period between additions can vary considerably and controlling the reaction temperature can be more difficult. From an operations view, the new method of adding aniline to butyraldehyde followed by the addition of the acetic acid catalyst can be beneficial. In prior production operations, it has been found that acetic acid can catalyze the self-condensation of butyraldehyde, and long addition times and/or poor cooling can significantly reduce the butyraldehyde available to react with aniline, which could lead to a reduction in DHP yield. Under production conditions, reversing the order of addition to add aniline to butyraldehyde followed by the addition of acetic acid provides for more reliably consistent yields

What is claimed is:

1. A method for producing 3,5-diethyl-1,2-dihydro-1-phenyl-2-propylpyridine, comprising the steps of
    a. creating a mixture of butyraldehyde, aniline, and acetic acid,
    b. heating the mixture to a first temperature of ≦50° C.,
    c. holding at the first temperature for a first period of time,
    d. heating the mixture to a second temperature of 70–80° C., and
    e. holding at the second temperature for a second period of time.]

2. The method of claim 1 wherein the first temperature is 40 to 45° C.

3. The method of claim 2 wherein the first temperature is about 40° C.,

4. The method of claim 3 wherein the first period of time is about one hour.

5. The method of claim 4 wherein the second temperature is about 75° C.

6. The method of claim 5 wherein the second period of time is about five hours.

7. The method of claim 1, further comprising the step of:
    a. heating the mixture to the reflux temperature subsequent to holding at the second temperature.

8. The method of claim 7, further comprising the step of:
    a. further purifying the 3,5-diethyl-1,2-dihydro-1-phenyl-2-propylpyridine.

9. The method of claim 7, further comprising the step of:
    a. adding a base to the mixture prior to heating to the reflux temperature.

10. The method of claim 9, further comprising the step of:
    a. adding a base to the mixture prior to heating to the reflux temperature.

11. The method of claim 10, wherein the base is sodium carbonate.

12. A method for producing 3,5-diethyl-1,2-dihydro-1-phenyl-2-propylpyridine, comprising the steps of:
    a. creating a mixture of butyraldehyde, aniline, and acetic acid,
    b. heating the mixture to form 3,5-diethyl-1,2-dihydro-1-phenyl-2-propylpyridine,
    c. adding a base to the mixture to neutralize the acetic acid, and
    d. heating the neutralized mixture to a reflux temperature.

13. The method of claim 12, further comprising the additional step of:
    a. purifying the 3,5-diethyl-1,2-dihydro-1-phenyl-2-propylpyridine.

14. The method of claim 12 wherein the heating step further comprises:
    a. heating to a first temperature for a first period of time; and
    b. heating to a second higher temperature for a second period of time.

15. The method of claim 14 wherein:
    a. the first temperature is <50° C.,
    b. the first period of time is at least 15 minutes,
    c. the second temperature is 70–80° C., and
    d. the second period of time is at least 2 hours.

16. A method for producing 3,5-diethyl-1,2-dihydro-1-phenyl-2-propylpyridine, comprising the steps of
    a. mixing butyraldehyde and aniline to create a mixture,
    b. subsequently adding acetic acid to the mixture of butyraldehyde and aniline, and
    c. heating the mixture to form 3,5-diethyl-1,2-dihydro-1-phenyl-2-propylpyridine.

17. The method of claim 16, wherein the heating step comprises:
    a. heating the mixture to a temperature below a reflux temperature and holding;
    b. and further comprising the step of heating the mixture to the reflux temperature subsequent to holding at the temperature below the reflux temperature.

18. The method of claim 17, further comprising the steps of:
    a. cooling the mixture, and
    b. removing a fraction containing 3,5-diethyl-1,2-dihydro-1-phenyl-2-propylpyridine.

* * * * *